US010022211B2

(12) United States Patent
Braido et al.

(10) Patent No.: US 10,022,211 B2
(45) Date of Patent: *Jul. 17, 2018

(54) VALVE HOLDER AND LOADING INTEGRATION (71) Applicant: St. Jude Medical, Cardiology Division, Inc., St. Paul, MN (US)

(72) Inventors: Peter N. Braido, Wyoming, MN (US); Jacob John Daly, Blaine, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 309 days.

This patent is subject to a terminal disclaimer.

(21) Appl. No.: 14/991,121

(22) Filed: Jan. 8, 2016

(65) Prior Publication Data
US 2016/0120632 A1    May 5, 2016

Related U.S. Application Data (63) Continuation of application No. 13/787,019, filed on Mar. 6, 2013, now Pat. No. 9,295,549.

(60) Provisional application No. 61/713,213, filed on Oct. 12, 2012.

(51) Int. Cl.
A61F 2/24 (2006.01)
A61F 2/00 (2006.01)
A61B 50/30 (2016.01)

(52) U.S. Cl.
CPC ............ A61F 2/0095 (2013.01); A61B 50/30 (2016.02); A61F 2/2418 (2013.01); A61F 2/2427 (2013.01); A61F 2230/008 (2013.01); A61F 2230/0054 (2013.01)

(58) Field of Classification Search
CPC .... A61F 2/0095; A61F 2/2418; A61F 2/2427; A61B 50/30; B65D 85/00
USPC ................................ 206/438, 363; 623/2.11
See application file for complete search history.

(56) References Cited

U.S. PATENT DOCUMENTS

| 3,657,744 | A | 4/1972 | Ersek |
| 4,101,031 | A | 7/1978 | Cromie |
| 4,211,325 | A | 7/1980 | Wright |
| 4,423,730 | A | 1/1984 | Gabbay |
| 5,560,487 | A | 10/1996 | Starr |
| 5,720,391 | A | 2/1998 | Dohm et al. |
| 5,843,167 | A | 12/1998 | Dwyer et al. |

(Continued)

FOREIGN PATENT DOCUMENTS

| EP | 1129744 A1 | 9/2001 |
| EP | 1157673 A2 | 11/2001 |

(Continued)

OTHER PUBLICATIONS

Ruiz, Carlos, Overview of PRE-CE Mark Transcatheter Aortic Valve Technologies, Euro PCR, dated May 25, 2010.

(Continued)

Primary Examiner — Steven A. Reynolds
(74) Attorney, Agent, or Firm — Lerner, David, Littenberg, Krumholz & Mentlik, LLP (57) ABSTRACT A device for holding an implantable medical device includes a jar for receiving the implantable medical device, and a ring coupleable to the jar. The ring has a plurality of channels adapted to receive retaining features of the implantable medical device to stabilize the medical device within the jar.

20 Claims, 10 Drawing Sheets

(56) References Cited

U.S. PATENT DOCUMENTS

| | | | |
|---|---|---|---|
| 5,868,253 | A | 2/1999 | Krueger et al. |
| 5,924,424 | A | 7/1999 | Stevens et al. |
| 5,968,068 | A | 10/1999 | Dehdashtian et al. |
| 6,077,297 | A | 6/2000 | Robinson et al. |
| 6,199,696 | B1 * | 3/2001 | Lytle ............... A61F 2/0095 206/363 |
| 6,306,141 | B1 | 10/2001 | Jervis |
| 6,416,547 | B1 | 7/2002 | Erickson et al. |
| 6,623,518 | B2 | 9/2003 | Thompson et al. |
| 6,736,845 | B2 * | 5/2004 | Marquez ............. A61F 2/2412 623/2.11 |
| 6,814,746 | B2 | 11/2004 | Thompson et al. |
| 6,830,584 | B1 | 12/2004 | Seguin |
| 7,018,406 | B2 | 3/2006 | Seguin et al. |
| 7,311,730 | B2 | 12/2007 | Gabbay |
| 7,329,278 | B2 | 2/2008 | Seguin et al. |
| 7,510,572 | B2 | 3/2009 | Gabbay |
| 7,682,390 | B2 | 3/2010 | Seguin |
| 7,699,168 | B2 | 4/2010 | Ryan et al. |
| 7,803,185 | B2 | 9/2010 | Gabbay |
| 7,806,926 | B2 * | 10/2010 | Stobie ............... A61F 2/2427 623/2.11 |
| 7,819,915 | B2 | 10/2010 | Stobie et al. |
| 8,562,663 | B2 | 10/2013 | Mearns et al. |
| 9,192,469 | B2 | 11/2015 | Mearns et al. |
| 9,414,914 | B2 | 8/2016 | Duffy et al. |
| 9,414,917 | B2 | 8/2016 | Young et al. |
| 2003/0050694 | A1 | 3/2003 | Yang et al. |
| 2004/0210304 | A1 | 10/2004 | Seguin et al. |
| 2005/0137695 | A1 | 6/2005 | Salahieh et al. |
| 2005/0137697 | A1 | 6/2005 | Salahieh et al. |
| 2006/0015177 | A1 | 1/2006 | Quest et al. |
| 2006/0074484 | A1 | 4/2006 | Huber |
| 2006/0106415 | A1 | 5/2006 | Gabbay |
| 2006/0142848 | A1 | 6/2006 | Gabbay |
| 2006/0167468 | A1 | 7/2006 | Gabbay |
| 2006/0259120 | A1 | 11/2006 | Vongphakdy et al. |
| 2007/0010876 | A1 | 1/2007 | Salahieh et al. |
| 2007/0027534 | A1 | 2/2007 | Bergheim et al. |
| 2007/0043435 | A1 | 2/2007 | Seguin et al. |
| 2007/0055358 | A1 | 3/2007 | Krolik et al. |
| 2007/0073391 | A1 | 3/2007 | Bourang et al. |
| 2007/0088431 | A1 | 4/2007 | Bourang et al. |
| 2007/0112422 | A1 | 5/2007 | Dehdashtian |
| 2007/0162100 | A1 | 7/2007 | Gabbay |
| 2007/0168013 | A1 | 7/2007 | Douglas |
| 2007/0203575 | A1 | 8/2007 | Forster et al. |
| 2007/0239271 | A1 | 10/2007 | Nguyen |
| 2007/0244552 | A1 | 10/2007 | Salahieh et al. |
| 2008/0071369 | A1 | 3/2008 | Tuval et al. |
| 2008/0147179 | A1 | 6/2008 | Cai et al. |
| 2008/0147182 | A1 | 6/2008 | Righini et al. |
| 2008/0228264 | A1 | 9/2008 | Li et al. |
| 2009/0054975 | A1 | 2/2009 | del Nido et al. |
| 2009/0287290 | A1 | 11/2009 | Macaulay et al. |
| 2010/0004740 | A1 | 1/2010 | Seguin et al. |
| 2010/0217382 | A1 | 8/2010 | Chau et al. |
| 2010/0252470 | A1 | 10/2010 | Ryan et al. |
| 2010/0262231 | A1 | 10/2010 | Tuval et al. |
| 2010/0286768 | A1 | 11/2010 | Alkhatib |
| 2010/0298931 | A1 | 11/2010 | Quadri et al. |
| 2011/0147251 | A1 | 6/2011 | Hodshon et al. |
| 2011/0198244 | A1 | 8/2011 | Murad et al. |
| 2011/0214398 | A1 * | 9/2011 | Liburd ............... A01N 1/0263 53/467 |
| 2011/0224678 | A1 | 9/2011 | Gabbay |
| 2011/0295216 | A1 | 12/2011 | Miller |
| 2012/0226348 | A1 | 9/2012 | Lane et al. |
| 2012/0239142 | A1 | 9/2012 | Liu et al. |
| 2012/0290079 | A1 | 11/2012 | Murad et al. |
| 2014/0299498 | A1 | 10/2014 | Neal et al. |
| 2014/0331475 | A1 | 11/2014 | Duffy et al. |
| 2016/0278955 | A1 | 9/2016 | Liu et al. |

FOREIGN PATENT DOCUMENTS

| | | |
|---|---|---|
| WO | 2007071436 A2 | 6/2007 |
| WO | 08070797 A2 | 6/2008 |
| WO | 2009042196 A2 | 4/2009 |
| WO | 2010051025 A1 | 5/2010 |
| WO | 2010087975 A1 | 8/2010 |

OTHER PUBLICATIONS

Quaden et al., "Percutaneous aortic valve replacement: resection before implantation", pp. 836-840, European J. of Cardio-thoracic Surgery, 27 (2005).

International Search Report and Written Opinion for Application No. PCT/US2013/064201 dated Jan. 29, 2014.

* cited by examiner

VALVE HOLDER AND LOADING INTEGRATION

CROSS REFERENCE TO RELATED APPLICATION

This application is a continuation of U.S. patent application Ser. No. 13/787,019 filed Mar. 6, 2013, which claims the benefit of the filing date of U.S. Provisional Patent Application No. 61/713,213 filed Oct. 12, 2012, the disclosures of which are hereby incorporated herein by reference.

BACKGROUND OF THE INVENTION

The present invention relates to heart valve replacement and, in particular, to heart valve loading and storage. More particularly, the present invention relates to devices and methods for holding, transferring and deploying prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

Despite the various improvements that have been made to the collapsible prosthetic heart valve delivery process, conventional storage, transfer and delivery techniques suffer from some shortcomings. Ideally, prosthetic heart valves are properly packaged at the manufacturing facility to ensure that the arriving valve performs as intended, and that the design and the quality of the valve is not compromised during delivery. However, in conventional prosthetic heart systems, the valve may sometimes be damaged during delivery. In addition to physical damage of the prosthetic heart valve during shipping and handling, valves may also be contaminated as they are transferred from storage or during implantation in the patient.

There therefore is a need for further improvements to the devices, systems, and methods for transcatheter storage and delivery of collapsible prosthetic heart valves. Among other advantages, the present invention may address one or more of these needs.

SUMMARY OF THE INVENTION

A device for holding an implantable medical device may include a jar for receiving the implantable medical device and a ring coupleable to the jar, the ring having a plurality of channels adapted to receive retaining features of the implantable medical device to stabilize the medical device within the jar.

In some examples, the ring further comprises a plurality of openings through which a liquid may be drained from the jar. The jar may include a plurality of clips and the ring includes a plurality of indentations capable of mating with the clips to lock the ring to the jar. The plurality of clips may be evenly spaced about a circumference of the jar and the plurality of channels may extend radially in the ring. In some variations, the channels may extend circumferentially or may be angled. The plurality of channels may include three channels and may be adapted to receive a circular retaining feature of the implantable medical device.

The plurality of channels may be adapted to receive a diamond-shaped retaining feature of the implantable medical device. The plurality of channels may be adapted to receive a square-shaped retaining feature of the implantable medical device.

In some embodiments, a device for transporting an implantable medical device may include a ring coupleable to the implantable medical device, the ring having a plurality of channels adapted to receive retaining features of the implantable medical device. The ring may further include a plurality of openings through which a liquid may be drained from the jar. The plurality of channels may extend radially in the ring. The plurality of channels may include three channels.

BRIEF DESCRIPTION OF THE DRAWINGS

Various embodiments of the presently disclosed delivery system are described herein with reference to the drawings, wherein.

Various embodiments of the present invention will now be described with reference to the appended drawings. It is to be appreciated that these drawings depict only some embodiments of the invention and are therefore not to be considered limiting of its scope.

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient.

Figure 1:
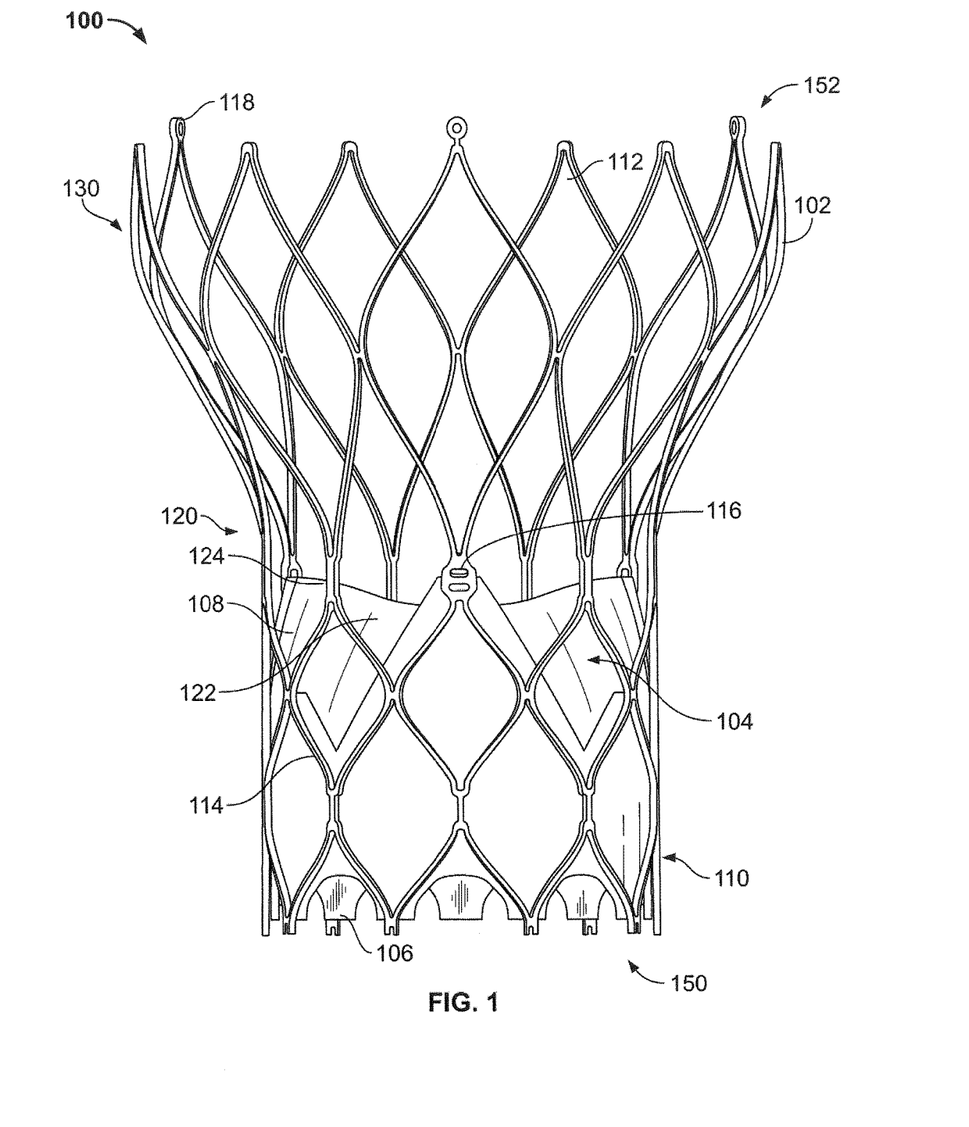
FIG. 1 is a side elevational view of a collapsible prosthetic heart valve showing the valve assembly attached to the stent.

FIG. 1 shows a collapsible prosthetic heart valve 100 according to an embodiment of the present disclosure. The prosthetic heart valve 100 is designed to replace the function of a native aortic valve of a patient. Examples of collapsible prosthetic heart valves are described in International Patent Application Publication No. WO/2009/042196; U.S. Pat. No. 7,018,406; and U.S. Pat. No. 7,329,278, the disclosures of all of which are hereby incorporated herein by reference. As discussed in detail below, the prosthetic heart valve has an expanded condition and a collapsed condition. Although the invention is described herein as applied to a prosthetic heart valve for replacing a native aortic valve, the invention is not so limited, and may be applied to prosthetic valves for replacing other types of cardiac valves.

The prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), ultra-high molecular weight polyethylene and polyaramides. The stent 102 may have an annulus section 110 adjacent a proximal end 150, an aortic section 130 adjacent a distal end 152, and a transition section 120 between the aortic section 130 and the annulus section 110. Each of the annulus section 110, the transition section 120 and the aortic section 130 of the stent 102 includes a plurality of struts 114. Certain struts 114 may be joined to form a plurality of cells 112 connected to one another around the stent. The annulus section 110 and the aortic section of the stent 102 may include one or more annular rows of cells 112 connected to one another. For instance, the annulus section 110 may have two annular rows of cells 112. The cells in the aortic section 130 may be larger than the cells in the annulus section 110. The larger cells in the aortic section 130 better enable the prosthetic valve 100 to be positioned without the stent structure interfering with blood flow to the coronary arteries. When the prosthetic heart valve 100 is in the expanded condition, each cell 112 may be substantially diamond shaped.

The annulus section 110 of stent 102 has a relatively small cross-section in the expanded condition, while the aortic section 130 has a relatively large cross-section in the expanded condition. Preferably, annulus section 110 is in the form of a cylinder having a substantially constant diameter along its length. The transition section 120 may taper outwardly from the annulus section 110 to the aortic section 130.

The stent 102 may also include a plurality of commissure features 116 for attaching the commissure between two adjacent leaflets to the stent. As can be seen in FIG. 1, the commissure features 116 may lie at the intersection of four cells 112, two of the cells being adjacent one another in the same annular row, and the other two cells being in different annular rows and lying in end-to-end relationship. Preferably, commissure features 116 are positioned entirely within annulus section 110 or at the juncture of annulus section 110 and transition section 120. Commissure features 116 may include one or more eyelets which facilitate the suturing of the leaflet commissure to the stent.

The prosthetic heart valve 100 also includes a valve assembly 104 attached inside the annulus section 110 of the stent 102. United States Patent Application Publication No. 2008/0228264, filed Mar. 12, 2007, and United States Patent Application Publication No. 2008/0147179, filed Dec. 19, 2007, the entire disclosures of both of which are hereby incorporated herein by reference, describe suitable valve assemblies. The valve assembly 104 may be wholly or partly formed of any suitable biological material or polymer. Examples of biological materials suitable for the valve assembly 104 include, but are not limited to, porcine or bovine pericardial tissue. Examples of polymers suitable for the valve assembly 104 include, but are not limited to, polyurethane, ultra-high molecular weight polyethylene and polyester.

The valve assembly 104 may be secured to stent 102 by any suitable attachment means, such as suturing, stapling, adhesives or the like. The valve assembly 104 includes a cuff 106 and a plurality of leaflets 108 which collectively function as a one-way valve. FIG. 1 illustrates a prosthetic heart valve for replacing a native tricuspid valve, such as the aortic valve. Accordingly, prosthetic heart valve 100 is shown in FIG. 1 with three leaflets 108, as well as three commissure features 116. However, it will be appreciated that the prosthetic heart valves according to this aspect of the invention may have a greater of lesser number of leaflets and commissure features.

Cuff 106 may be disposed on the lumenal surface of annulus section 110, on the ablumenal surface of annulus section 110, or on both surfaces, and the cuff may cover all or part of either or both of the lumenal and ablumenal surfaces of the annulus section. FIG. 1 shows cuff 106 disposed on the lumenal surface of annulus section 110 so as to cover part of the annulus section while leaving another part thereof uncovered. The cuff 106 may be wholly or partly formed of any suitable biological material or polymer, such as ultra-high molecular weight polyethylene or PTFE.

A first edge (not shown) of each leaflet 108 may be attached to the stent 102 by any of the various manners described above. For example, the first edge of each leaflet 108 may be sutured to the stent 102 by passing strings or sutures through the cuff 106 of the valve assembly 104. The cuff and/or sutures may be formed from ultra-high-molecular-weight polyethylene. A second or free edge 124 of each leaflet 108 may coapt with the corresponding free edges of the other leaflets, thereby enabling the leaflets to function collectively as a one-way valve.

As is shown in FIG. 1, the entirety of valve assembly 104, including the leaflet commissures, may be positioned in the annulus section 110 of stent 102. When opened, the leaflets may extend further into the transition section or may be designed such that they remain substantially completely within the annulus section. That is, substantially the entirety of valve assembly 104 may be positioned between the proximal end 150 of stent 102 and the commissure features 116, with none of the valve assembly 104 positioned between commissure features 116 and the distal end 152 of the stent.

It will also be noted that while the inventions herein described are predominately discussed in terms of a tricuspid valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Stent 102 may include one or more retaining elements 118 at the distal end 152 thereof, the retaining elements being sized and shaped to cooperate with female retaining recesses provided on a deployment or storage device. Additionally, the retaining elements 118 may be disposed at the proximal end 150 of the device or on both ends of the device. The engagement of retaining elements 118 with the female retaining recesses on the deployment device helps maintain prosthetic heart valve 100 in assembled relationship with the deployment or storage device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and during deployment.

In operation, the embodiments of the prosthetic heart valve described above may be used to replace a native heart valve, such as the aortic valve, a surgical heart valve or a heart valve that has undergone a surgical procedure. The prosthetic heart valve may be delivered to the desired site (e.g., near a native aortic annulus) using any suitable delivery device. During delivery, the prosthetic heart valve is disposed inside the delivery device in the collapsed condition. The delivery device may be introduced into a patient using a transfemoral, transapical, transseptal, transaxillary or any other percutaneous approach. Once the delivery device has reached the target site, the user may deploy the prosthetic heart valve. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction.

In a prosthetic heart valve, the valve assembly may be spaced from the distal or aortic end of the stent by a distance that enables deployment of the heart valve by an amount sufficient for the valve leaflets of the prosthetic valve to operate as intended, while the distal end 152 of the stent remains captured by the delivery device. More particularly, as will be explained further below, the annulus end of the prosthetic heart valve may be deployed first while the aortic end of the prosthetic heart valve remains at least partially covered by the distal sheath of the delivery device. The annulus portion of the prosthetic heart valve may be deployed so that the entirety of the valve leaflets, up to and including the commissures, is deployed and fully operational. By deploying the prosthetic heart valve in this manner, the user can determine whether the valve leaflets are properly positioned relative to the native valve annulus, and whether the valve is functioning properly. If the user determines that the position and operation of the valve are acceptable, the remainder of the valve may be deployed. However, if it is determined that the leaflet position is improper or that the valve is not functioning properly, the user may resheath the valve and either reposition it for redeployment, or remove it entirely from the patient. This can be particularly important in very high risk patients who would typically be recipients of these types of valves, because of the nature of their condition and the impact that may have on the shape and/or condition of the native valve and valve annulus.

Figure 2:
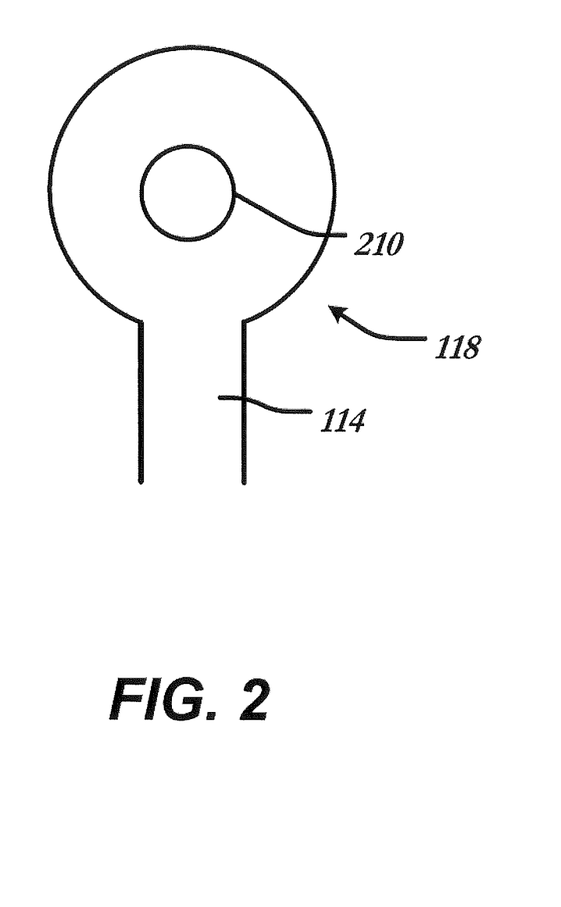
FIG. 2 is an enlarged side elevational view of a retaining element of a collapsible prosthetic heart valve.

FIG. 2 is an enlarged view of the retaining element 118 described in FIG. 1, above. As shown in FIG. 2, one or more struts 114 may terminate in a circular retaining element 118. Retaining element 118 may include an eyelet 210 used to position, transfer or adjust the position of the stent via a snare as will be described later. Retaining elements 118 may also be useful in implanting the heart valve 100 in a patient by mating to a delivery device as described above with reference to FIG. 1.

Figure 3A:
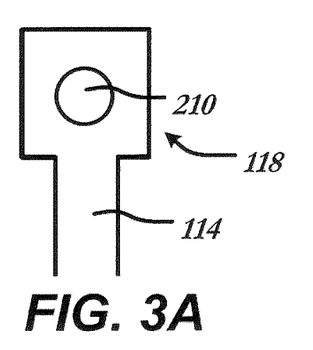
FIGS. 3A-E are enlarged side elevational views of alternate embodiments of retaining elements.
Figure 3B:
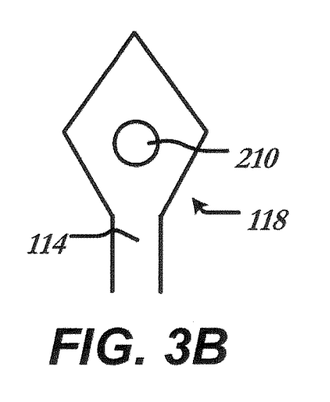
Figure 3C:
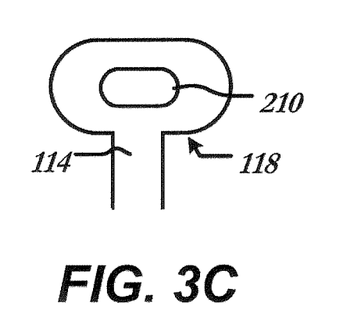

FIGS. 3A-E illustrate several variations of the retaining element shown in FIG. 2 to aid in storage, shipment, transfer and delivery of a prosthetic heart valve. FIG. 3A illustrates a first example of a retaining element 118 at the end of a strut 114, the retaining element 118 being in the shape of a square. As with the retaining element shown in FIG. 2, square retaining element 118 may include one or more eyelets 210. It will be understood that eyelet 210 need not be circular and that various configurations of the eyelet, such as oval, triangular and square eyelets are contemplated. FIG. 3B illustrates a diamond-shaped retaining element 118 attached to a strut 114, the retaining element having an eyelet 210. FIG. 3C illustrates an oblong retaining element 118 having an elongated eyelet 210.

Figure 3D:
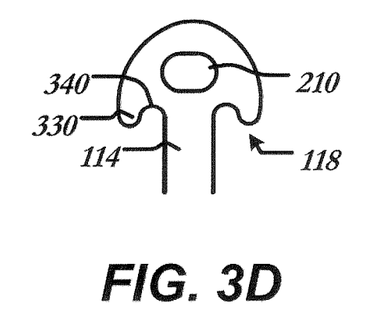
Figure 3E:
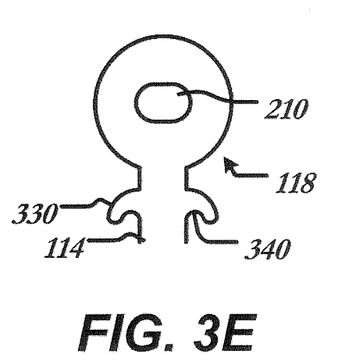

FIG. 3D illustrates a substantially semi-circular retaining element 118 having a circular eyelet 210. Retaining element 118 may further include a pair of tabs 330 that form recesses 340 between tabs 330 and strut 114. Recesses 340 may be used as additional members for snaring the stent during repositioning, loading and/or delivery. FIG. 3E illustrates yet another example of retaining element 118. The retaining element 118 of FIG. 3E is circular in form but also includes a pair of separate tabs 330 similar to those described in FIG. 3D. In contrast to the example shown in FIG. 3D, tabs 330 are formed as part of strut 114 and not as part of retaining element 118. As previously discussed, retaining element 118 may mate with female recesses on a deployment or delivery device. Thus, by forming tabs 330 on strut 114 instead of on retaining element 118, the same deployment or storage devices may be used to couple to the stents regardless of whether they include tabs 330.

Figure 4:
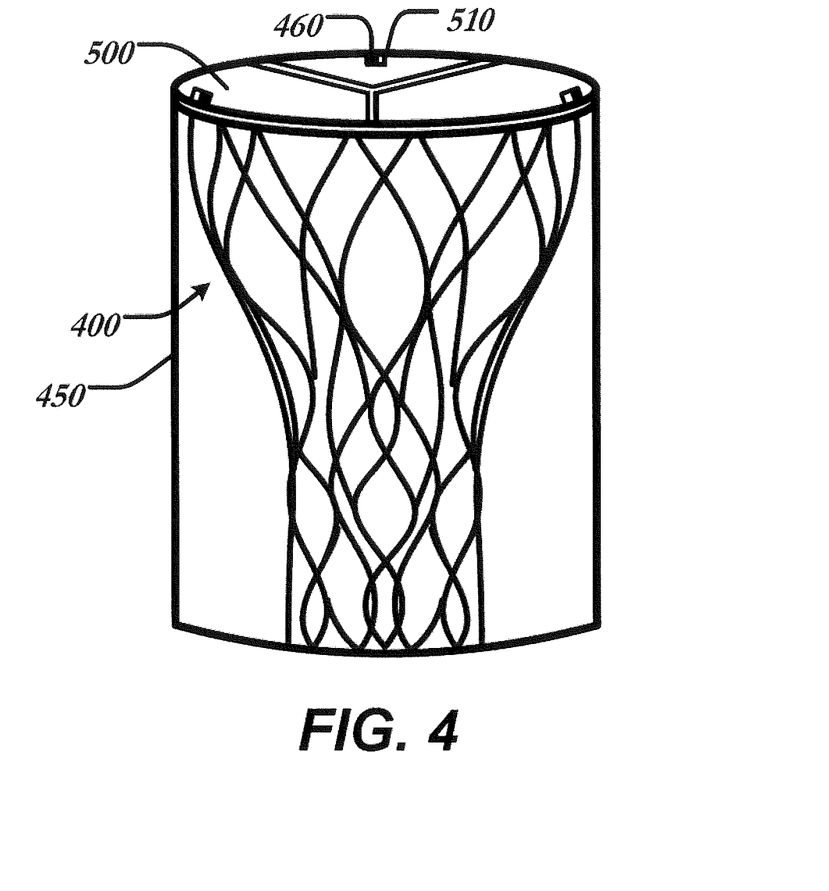
FIG. 4 is a diagrammatic view of a stent disposed within a jar for storage and/or transport.

FIG. 4 illustrates one method of storing and transporting a stent within a jar. As seen in FIG. 4, jar 450 may be sized slightly larger than stent 400 and stent 400 may be placed in an upright position within the jar. A ring 500 may be placed on top of jar 450 to keep the stent 400 from moving during delivery and/or storage. An additional top cap (not shown) may be disposed on top of ring 500 to seal and secure stent 400 within jar 450.

Jar 450 may include a plurality of clips 460 which mate with a plurality of indentations 510 on ring 500 to align the ring with jar 450. Clips 460 may also help secure ring 500 to jar 450. Clips 460 may be pliable prongs that are simply bent over selected indentations of the ring. Alternatively, clips 460 may include spring clips which deform from an initial position to facilitate mating with the indentations, and then spring back into their original position within the indentations to hold the ring 500 in place. Additional sutures may also be used to secure the stent. The jar may be filled with a preserving solution that immerses stent 400, such as glutaraldehyde, formaldehyde or an inert gas such as nitrogen.

Figure 5:
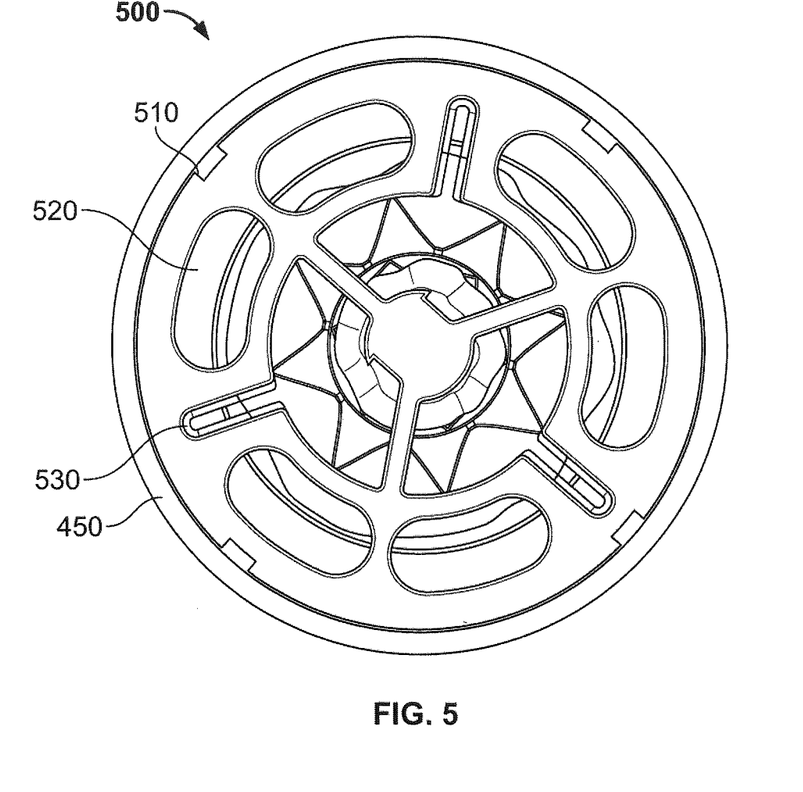
FIG. 5 is a top view of a ring coupled to a jar containing the stent.

FIG. 5 illustrates a top view of ring 500 coupled to jar 450. In the illustrated example, ring 500 includes three indentations 510 for aligning it with jar 450. Ring 500 may further include a plurality of openings 520 to allow drainage of the preserving solution from jar 450 after removal of the top cap. Any number of openings 520 may be formed in ring 500 and the shape and size of the openings may be varied as desired. Ring 500 may further include a plurality of channels 530 adapted to receive the retaining elements 118 described above. The number of channels 530 may be the same as the number of retaining elements 118 on stent 102. Channels 530 may be evenly spaced about the perimeter of ring 500 when retaining elements 118 are evenly spaced around the perimeter of stent 400. As illustrated, ring 500 includes three channels 530, although it will be understood that the ring may include two, three, four, five, six or more channels.

Figure 6A:
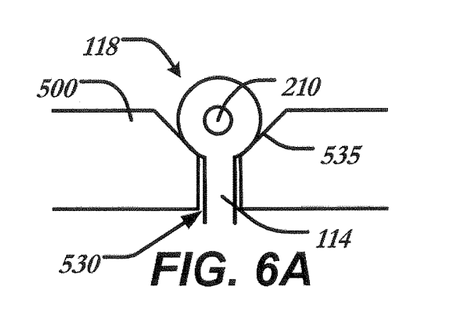
FIGS. 6A-6D is a series of retainer element-channel interfaces coupling the stent to a ring.
Figure 6B:
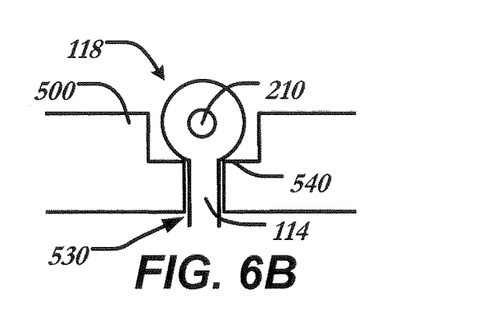
Figure 6C:
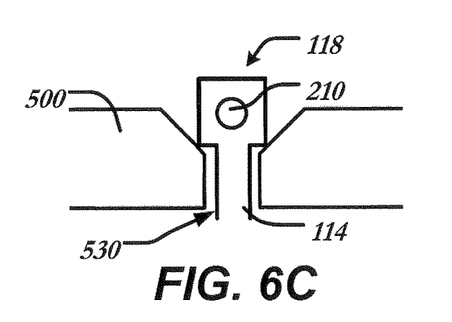
Figure 6D:
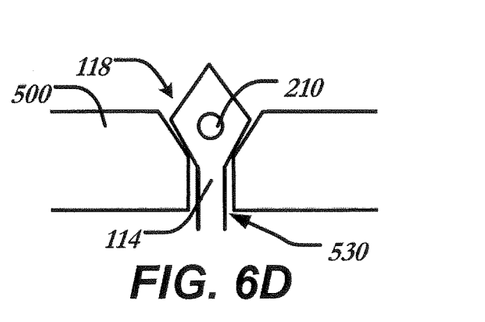

The cross-sectional shape of channels 530 may be varied, and may be dependent upon the shape of the retaining elements 118 to be received therein. FIGS. 6A-6D illustrate a series of retaining element-channel interfaces. FIG. 6A illustrates a retaining element 118 similar to that shown in FIG. 2 within a channel 530 of ring 500. Channel 530 may include a beveled top surface 535 to properly locate and seat retaining element 118 in the channel. The same or similar retaining element 118 may also mate with a channel 530 having a square recess 540 in its top surface, as seen in FIG. 6B. In other examples illustrated in FIGS. 6C and 6D, channels 530 may have a beveled top surface for accepting square or diamond-shaped retaining elements 118. It will be appreciated that the bevel angle illustrated in FIG. 6D is steeper than that of FIG. 6C. Thus, the angle of the bevel of channel 530 may be selected to accommodate various retaining elements 118.

In operation, a fully assembled prosthetic heart valve 100 may be placed in a jar 450 having glutaraldehyde or other preserving solution. Ring 500 may be correctly positioned over jar 450 by aligning the clips 460 of the jar with the indentations 510 of the ring. Certain struts 114 of heart valve 400 that include retaining elements 118 may be guided into channels 530 of ring 500 and allowed to naturally radially expand until the retaining elements are affixed within the channels. Once all retaining elements 118 are mated within ring 500, a top cap, such as a screw cap, may be affixed to jar 450 to seal heart valve 400 within the jar. Jar 450 may then be transported to a hospital or clinic for use.

Once at the use location, the prosthetic heart valve 400 may be removed from jar 450 as will be described below. Ideally, prosthetic heart valve 400 is removed from jar 450 using aseptic techniques to maintain sterility and avoid contamination of the valve.

Figure 7A:
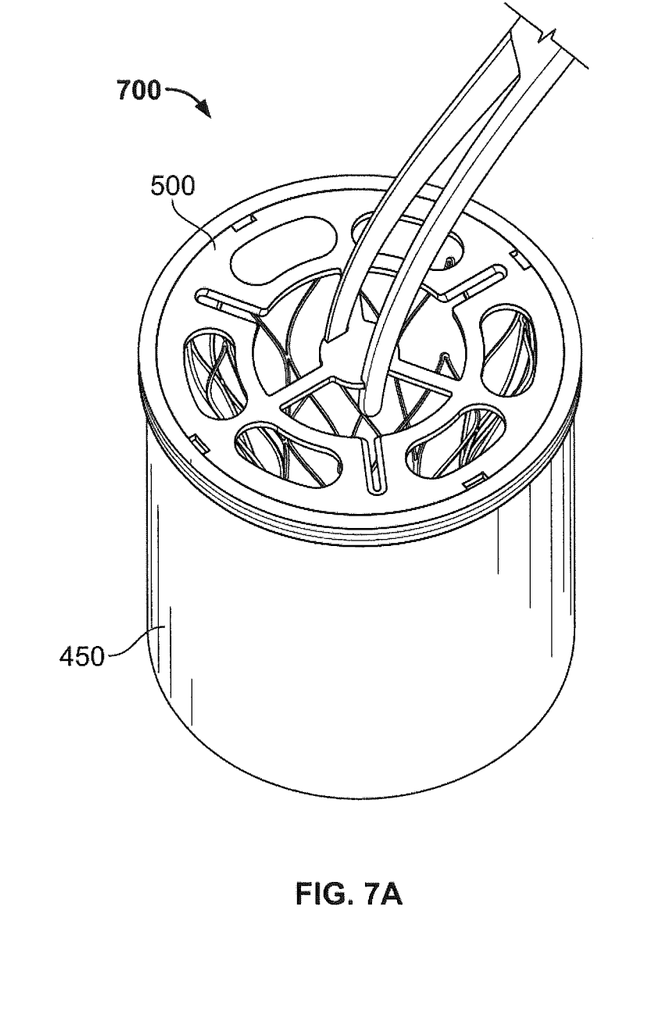
FIG. 7A is a partial perspective view of a tool for decoupling the ring from the jar.

A tool 700 may be used to detach ring 500 from jar 450. FIG. 7A illustrates the use of tweezers to pull ring 500 off jar 450. It will be understood that a hemostat, forceps, clamp or other similar instrument may likewise be used to remove ring 500 from jar 450 or that manual removal of ring 500 using fingers may be possible. As seen in FIG. 7A, tool 700 grasps a portion of ring 500 and pulls it to decouple it from jar 450, disengaging clips 460 from indentations 510.

Figure 7B:
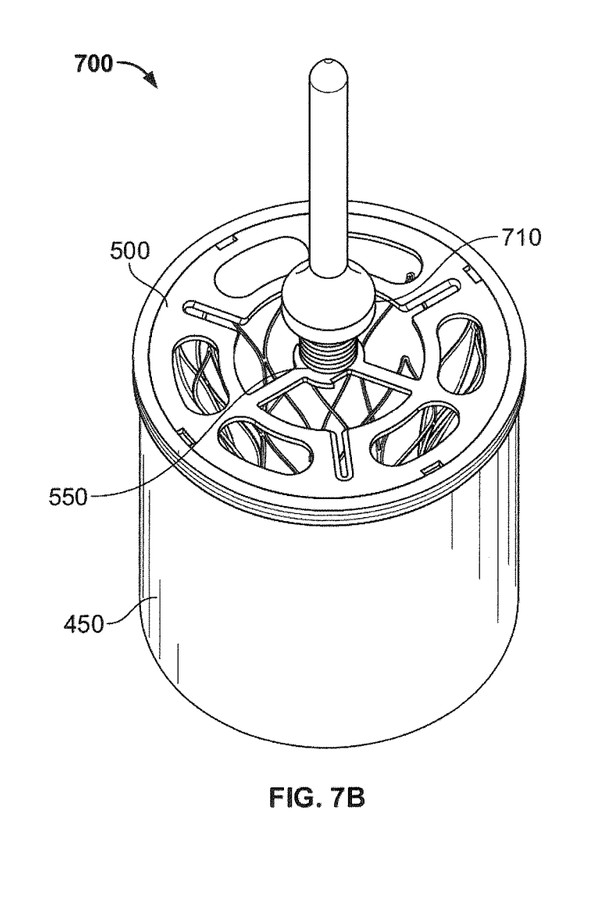
FIG. 7B is a partial perspective view of a tool and a threaded shaft for decoupling the ring from the jar.
Figure 7C:
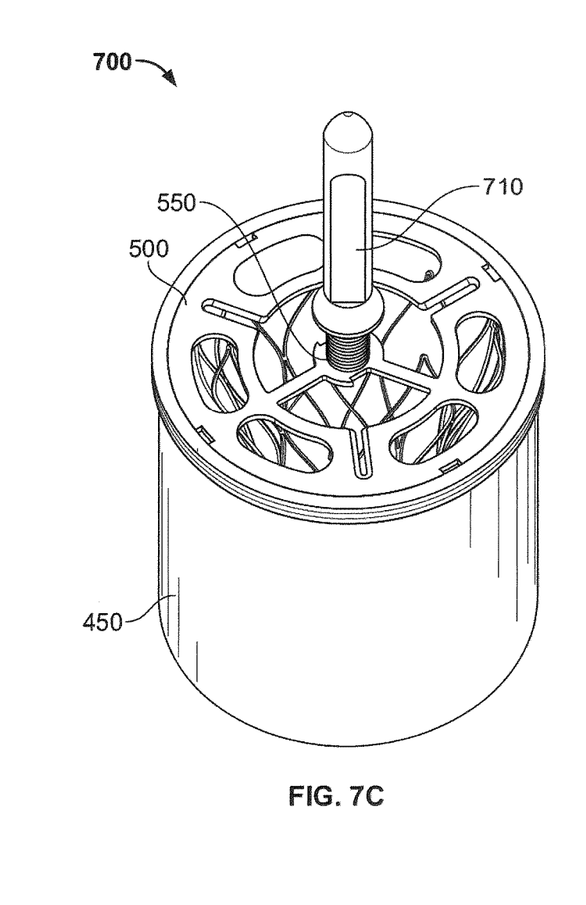
FIG. 7C is a partial perspective view of a press-fit shaft for decoupling the ring from the jar.

FIG. 7B shows a similar concept, but includes a tool having a threaded shaft 710 that mates with a threaded aperture 550 in the center of ring 500. Instead of being threaded, shaft 710 may instead be press-fit or snap fit into a non-threaded aperture in the center of ring 500 to remove the ring from the jar as seen in FIG. 7C.

Figure 7D:
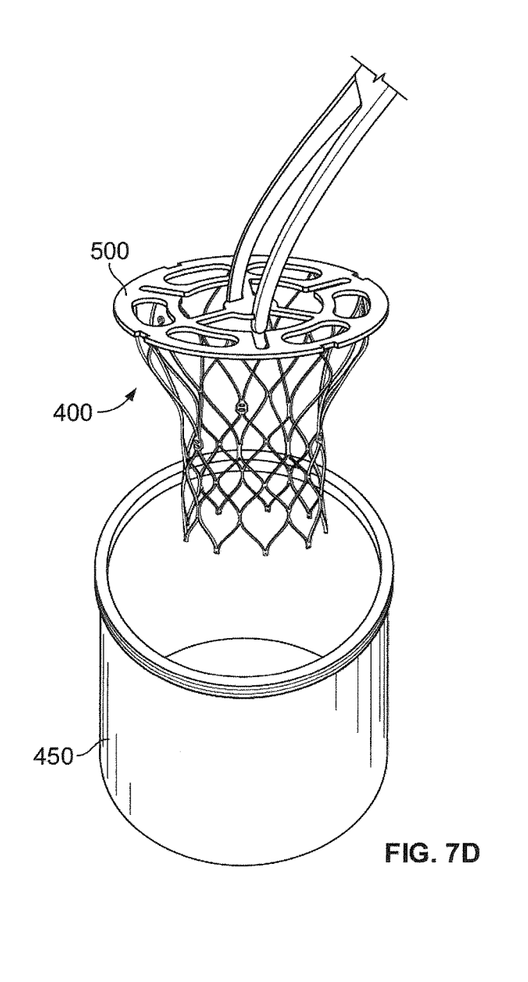
FIG. 7D is a perspective view showing a ring being decoupled from the jar.

Regardless of the method of detachment, once ring 500 is decoupled from jar 450, prosthetic heart valve 400 remains attached to ring 500 via the retaining elements 118. FIG. 7D illustrates a stent 400 coupled to a ring 500 being removed from jar 450. For the sake of clarity, stent 400 does not include a valve assembly, although it will be understood that a completely assembled prosthetic heart valve 400 includes a valve assembly.

Figure 7E:
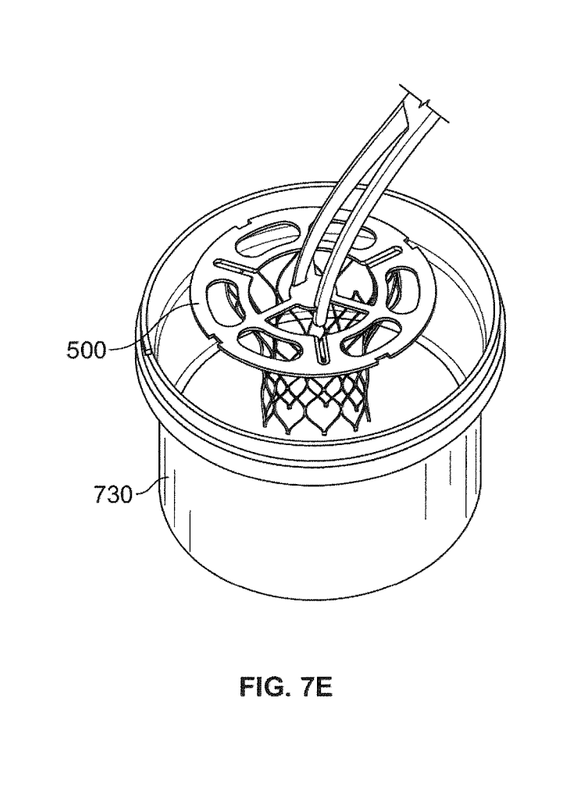
FIG. 7E is a perspective view showing the heart valve being rinsed.

Prosthetic heart valve 400 may be rinsed in a solution 730 while still being secured to ring 500, as shown in FIG. 7E. The rinsing solution may, for example, include a 0.9% sterile saline solution. Heart valve 400 may be immersed in rinsing solution 730 simply by grasping ring 500, without the need to contact the valve, thereby reducing the likelihood of contamination and damage to the prosthetic heart valve.

Figure 7F:
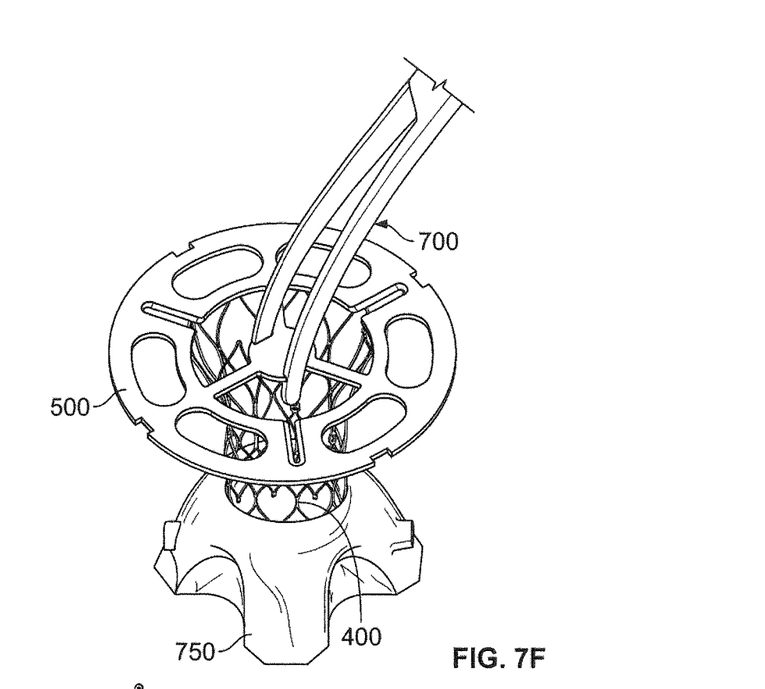
FIG. 7F is a perspective view showing the heart valve being inserted into the support member of a valve loading device.
Figure 7G:
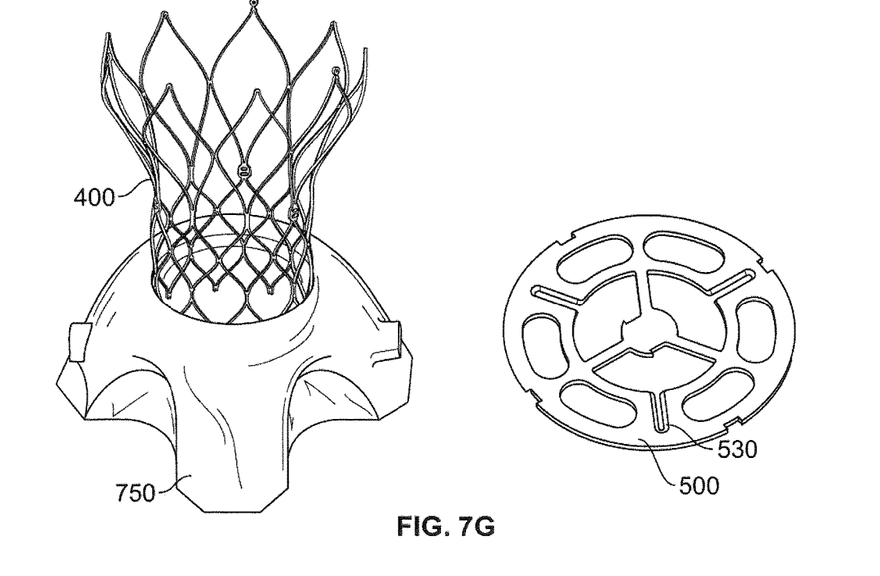
FIG. 7G is a partial perspective view showing a heart valve inserted in the support member with the ring removed.

Using tool 700, ring 500 may be maneuvered to place prosthetic heart valve 400 in a support member 750 of a valve loading system, as seen in FIG. 7F. At this juncture, retaining elements 118 of heart valve 400 may be decoupled from channels 530 of ring 500 by sliding each retaining element 118 radially inward until it clears its associated channel 530. The retaining elements 118 may be decoupled from the channels 530 together or one at a time. FIG. 7G illustrates heart valve 400 after being loaded into support member 750 and removal of ring 500. Prosthetic heart valve 400 may now be ready for loading into a delivery device using the valve loading system. Thus, heart valve 400 may be shipped, transferred and loaded with minimal handing.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A kit for storing an implantable medical device, the kit comprising:
   an implantable medical device including a collapsible and expandable prosthetic heart valve having i) a compressible stent having an inflow end and an outflow end, and ii) a valve assembly configured to permit a blood flow in a first direction from the inflow end to the outflow end, and to impede the blood flow in an opposite direction;
   a jar for receiving the implantable medical device; and
   a ring coupleable to an open end of the jar, the ring having outer and inner circumferences and a plurality of channels adapted to receive a portion of the outflow end of the implantable medical device to stabilize the medical device within the jar.

2. The kit of claim 1, wherein the ring further comprises a plurality of openings through which a liquid may be transferred.

3. The kit of claim 1, wherein the jar includes a plurality of clips and the ring includes a plurality of indentations capable of mating with the clips to lock the ring to the jar.

4. The kit of claim 3, wherein the plurality of clips are evenly spaced about a circumference of the jar.

5. The kit of claim 1, wherein the plurality of channels extend radially in the ring.

6. The kit of claim 1, wherein the plurality of channels include three channels.

7. The kit of claim 1, wherein the plurality of channels are adapted to receive circular retaining features of the implantable medical device.

8. The kit of claim 1, wherein the plurality of channels are adapted to receive diamond-shaped retaining features of the implantable medical device.

9. The kit of claim 1, wherein the plurality of channels are adapted to receive square-shaped retaining features of the implantable medical device.

10. A system for transporting an implantable medical device, the system comprising:
    an implantable medical device including a collapsible and expandable prosthetic heart valve having i) a compressible stent having an inflow end and an outflow end, and ii) a valve assembly configured to permit a blood flow in a first direction from the inflow end to the outflow end, and to impede the blood flow in an opposite direction;

a ring coupleable to the implantable medical device and having outer and inner circumferences and a plurality of channels adapted to receive a portion of the outflow end of the implantable medical device.

11. The system of claim 10, wherein the ring further includes a plurality of openings through which a liquid may flow.

12. The system of claim 10, wherein the plurality of channels extends radially in the ring.

13. The system of claim 10, wherein the plurality of channels includes three channels.

14. The system of claim 10, wherein the stent includes retaining features for coupling to a delivery device, the retaining features being coupleable to the plurality of channels of the ring.

15. The system of claim 10, wherein the outer circumference of the ring is uninterrupted by the plurality of channels.

16. The system of claim 10, wherein the ring defines a plurality of inner voids, each of the plurality of inner voids being in communication with one of the channels adjacent a center of the ring.

17. A system for transporting an implantable medical device, the system comprising:

an implantable medical device including a collapsible and expandable prosthetic heart valve having i) a compressible stent, and ii) a valve assembly configured to permit a blood flow in a first direction from an inflow end to an outflow end, and to impede the blood flow in an opposite direction;

a ring coupleable to the implantable medical device and having inner and outer circumferences and a plurality of inner voids and a plurality of channels, each of the plurality of channels extending radially from one of the plurality of voids toward the outer circumference of the ring and terminating before the outer circumference of the ring, and being adapted to receive a portion of the outflow end of the implantable medical device, each of the plurality of inner voids being in communication with one of the channels adjacent a center of the ring.

18. The system of claim 17, wherein the plurality of channels extend radially in the ring.

19. The system of claim 17, wherein the plurality of channels include three channels.

20. The system of claim 17, wherein the plurality of channels are adapted to receive circular retaining features of the implantable medical device.

* * * * *